(12) United States Patent
Little

(10) Patent No.: US 7,740,578 B2
(45) Date of Patent: Jun. 22, 2010

(54) DIRECT READING ENDOSCOPIC MEASURING INSTRUMENT AND METHOD

(76) Inventor: Paul K. Little, 7410 Cannock Rd., Richmond, VA (US) 23832

( * ) Notice: Subject to any disclaimer, the term of this patent is extended or adjusted under 35 U.S.C. 154(b) by 964 days.

(21) Appl. No.: 11/358,555

(22) Filed: Feb. 21, 2006

(65) Prior Publication Data

US 2007/0197863 A1 Aug. 23, 2007

(51) Int. Cl.
*A61B 5/107* (2006.01)
*A61B 5/103* (2006.01)

(52) U.S. Cl. ........................ 600/117; 600/104; 600/587; 600/591; 606/113; 606/110; 606/128; 606/1

(58) Field of Classification Search .................. 600/106, 600/104, 591, 117, 587; 700/164; 33/20.1; 606/113, 110, 128, 127
See application file for complete search history.

(56) References Cited

U.S. PATENT DOCUMENTS

| | | | |
|---|---|---|---|
| 3,706,307 A * | 12/1972 | Hasson | ........................ 600/591 |
| 3,817,635 A | 6/1974 | Kawahara | |
| 3,819,267 A | 6/1974 | Kawahara | |
| 4,558,691 A | 12/1985 | Okada | |
| 4,608,965 A | 9/1986 | Anspach, Jr. et al. | |
| 4,685,474 A * | 8/1987 | Kurz et al. | .................. 600/591 |
| 4,702,229 A | 10/1987 | Zobel | |
| 5,058,603 A | 10/1991 | Doi et al. | |
| 5,113,846 A | 5/1992 | Hiltebrandt | |
| 5,967,968 A | 10/1999 | Nishioka | |
| 6,033,359 A * | 3/2000 | Doi | ........................... 600/117 |
| 6,450,976 B2 | 9/2002 | Korotko et al. | |
| 6,458,076 B1 * | 10/2002 | Pruitt | .......................... 600/146 |
| 6,613,002 B1 | 9/2003 | Clark et al. | |
| 6,814,728 B2 | 11/2004 | Ouchi | |
| 6,890,296 B2 | 5/2005 | Ogawa | |
| 2002/0026093 A1 | 2/2002 | Ooyatsu | |
| 2003/0225419 A1 * | 12/2003 | Lippitt et al. | ................ 606/127 |
| 2004/0019255 A1 | 1/2004 | Sakiyama | |
| 2004/0220555 A1 * | 11/2004 | Abe | .............................. 606/1 |
| 2005/0171402 A1 * | 8/2005 | Cohen et al. | ................. 600/154 |

* cited by examiner

*Primary Examiner*—Linda C Dvorak
*Assistant Examiner*—Tina Nguyen
(74) *Attorney, Agent, or Firm*—Thomas, Karceski, Raring & Teague, PC

(57) ABSTRACT

The invention relates to a direct reading endoscopic measuring instrument and, more specifically, to a manually operated measuring instrument that is placed in close proximity to an internal anatomical feature and a related method for operation of the measuring instrument. The direct reading endoscopic measuring instrument includes a distal reticule that is passed through an endoscope in a folded position. When extended past the distal end of the endoscope proximate to an anatomical structure to be measured, a remote actuator unfolds the reticule along an axis perpendicular to the endoscope. Graduations on the reticule can be observed to directly measure the size of the anatomical structure.

14 Claims, 4 Drawing Sheets

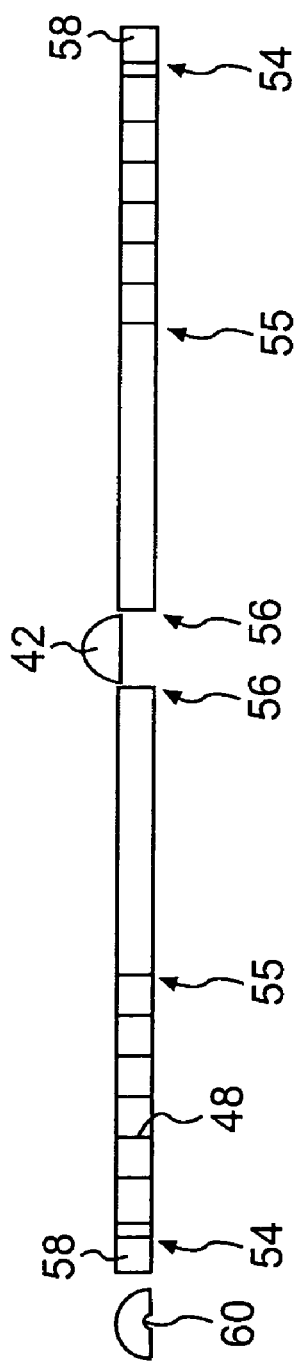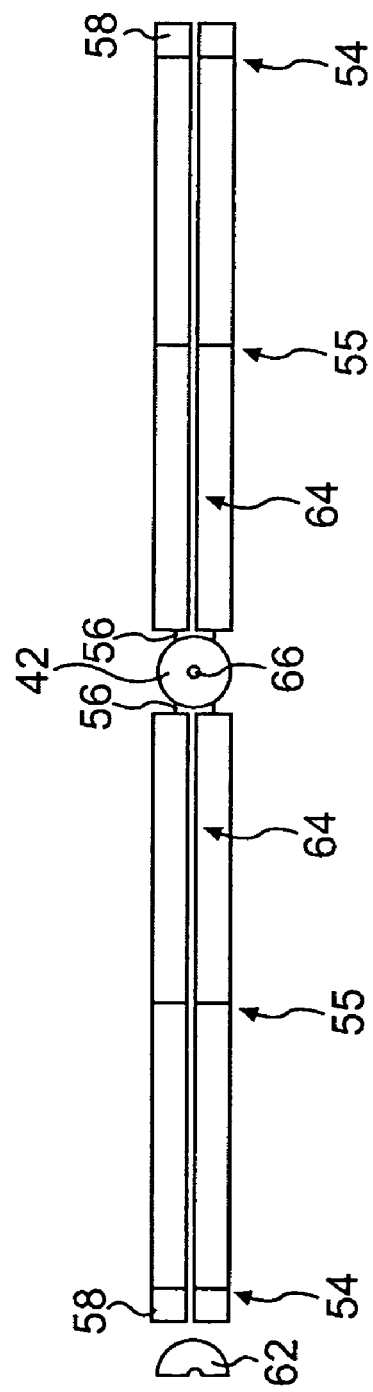

DIRECT READING ENDOSCOPIC MEASURING INSTRUMENT AND METHOD

The present invention relates to a direct reading endoscopic measuring instrument and, more specifically, to a manually operated measuring instrument that is placed in close proximity to an internal anatomical feature and a related method for operation of the measuring instrument.

BACKGROUND

With advances in optics and miniaturized assembly techniques, endoscopes now play a vital role in modern medicine. Endoscopes are flexible surgical tools used to introduce mechanical instruments, fluids, viewing instruments, and the like into a body. An endoscope, which generally has a tubular shape, is fed into an opening or incision in a body until the distal end of the endoscope is proximate a site to be observed or operated on. The interior of the endoscope includes one or more bores or lumens. These lumens act as passages for various instruments or tools that facilitate diagnostic or therapeutic procedures. For instance, a fiber optic cable with an optical lens (camera) can be integral to the endoscope or extended the length of the endoscope. The camera is operable to view the tissue proximate to the distal end of the endoscope. Other lumens can be used to provide light, fluids, mechanical surgical tools, or the like. Endoscopes are extremely useful to observe or biopsy internal organs such as the colon, bladder, stomach, lungs, liver, or the like. Overall, endoscopes have revolutionalized many procedures by giving the operating doctor much greater information from, and access to, internal structures without an invasive procedure. Doctors can now observe and diagnose organs and joints with minimal impact.

One area where endoscopes are used routinely is in the observation and measurement of tumors, internal growths, or other anatomical structures (ulcers, tears, scars, etc.). The size of such structures can be measured in a variety of ways. For instance, it is known to place graduations onto the camera lens of a fiber optic camera placed within an endoscope. Although the graduation measurements on the lens may be known, it is only possible to estimate the size of the internal structure because the distance from the lens to the structure is unknown. This type of measurement technique does not provide the depth of the structure. Another common solution is to electronically calculate the size of a structure. To accomplish this, a tool with uneven graduations will be placed near a structure. The observation equipment calculates a size scale to correct for the uneven graduations. This approach is generally expensive, overly complex, and not entirely accurate. Typically, this calculated method, as opposed to a direct reading method, will only measure the structure in one direction.

Measurement tools are known to have unevenly spaced graduations that are formed at a tip end portion of a flexible shaft. The shaft is detachably inserted through an instrument tool channel in an endoscope. The shaft is placed next to the structure, and can be observed via a camera. Again, the size of an internal structure can only be measured in one direction. The orientation of the shaft prohibits measurements in two directions. So while it is thought to be an improvement to have a direct reading tool, it is also thought to be nearly impossible to directly measure the dimensions of an object in two different directions with such a tool. Moreover, the known tools may require more than one measuring instrument, endoscope, or are otherwise overly complex. Direct reading tools may not take measurements along an axis perpendicular to the endoscope.

As such, there is a clear need within the medical industry for an inexpensive, easy to operate, simple, durable, and selectively removable direct reading endoscopic measurement instrument ('DREMI'). Ideally, the DREMI provides accurate measurements of internal structures in at least one direction, including along an axis perpendicular to the endoscope. The apparatus and method of the present invention would effectively address shortcomings as known in the prior art.

SUMMARY OF THE INVENTION

In accordance with the present invention, a DREMI, and method for operating the DREMI, are provided that include a manually operated measuring instrument that is placed in close proximity to an internal anatomical feature. The DREMI is inserted into a body, such as a human body, through an endoscope. When the DREMI is properly positioned, a reticule is unfolded proximate to an anatomical structure. Using evenly spaced graduations on the reticule, an operator can directly measure the structure via an endoscopic camera, as known in the art, that is included in the endoscope.

The distal reticule provided by the DREMI is extended past the distal (inserted) end of the endoscope in a folded condition. A manual actuator, as known in the art, is operable to unfold the distal reticule proximate to the anatomical feature once the reticule has exited the endoscope. In the unfolded state, the distal reticule is substantially perpendicular to the axis of the endoscope. The graduations on the DREMI allow an attendant, physician or other operator to directly measure the size of the anatomical feature in question in at least one direction, including along an axis perpendicular to the endoscope.

The DREMI includes the manual actuator, a coil pipe with an actuator wire, and the distal reticule wherein the actuator wire connects the actuator to the unfoldable distal reticule. The coil pipe and folded distal reticule are inserted into a channel provided by an endoscope, either before or after the endoscope is positioned with the body. The actuator is external to both the body and endoscope for actuation by an operator. The size and length of the DREMI will be determined, in part, by the size and length of the endoscope being used for the particular medical procedure that is to be performed. The reticule is naturally biased into the folded position.

In a preferred embodiment, the actuator is a commonly used slide trigger that is secured to both the proximal end of the coil pipe and to an actuator wire for selectively unfolding the distal reticule. Sliding the trigger towards the coil pipe along the length of the actuator operates to retract the actuator wire at the distal reticule. Retracting the actuator wire causes the reticule to unfold when the reticule has been passed out of the distal end of the endoscope. Other types of actuators are available, and the structure of the actuator and direction of activation are not important to the present invention.

In one preferred embodiment, the reticule includes evenly spaced graduations along at least a portion of the length of the reticule. The graduations are visible in both the unfolded and folded states via an endoscopic camera. In this manner, the DREMI can be used to measure an anatomical structure in at least one direction, including along an axis perpendicular to the endoscope. The image from the endoscopic camera does not need to be scaled.

A DREMI and the related method of operation in accordance with the present invention efficiently address at least one of the shortcomings associated with prior art endoscopic measuring devices. The foregoing and additional features and advantages of the present invention will become apparent to those of skill in the art from the following detailed description of a preferred embodiment taken in conjunction with the accompanying drawings.

BRIEF DESCRIPTION OF THE DRAWINGS

FIG. 5 is a side view of the reticule provided by the DREMI wherein the reticule is spread apart along the length of the reticule; and FIG. 6 is a bottom view thereof.

DETAILED DESCRIPTION

A DREMI in accordance with the present invention provides the medical industry with an inexpensive, easy to operate, simple, durable, and selectively removable direct reading endoscopic measurement instrument. The DREMI provides accurate measurements of internal structures in at lease one direction, including along an axis perpendicular to the endoscope.

Figure 1:
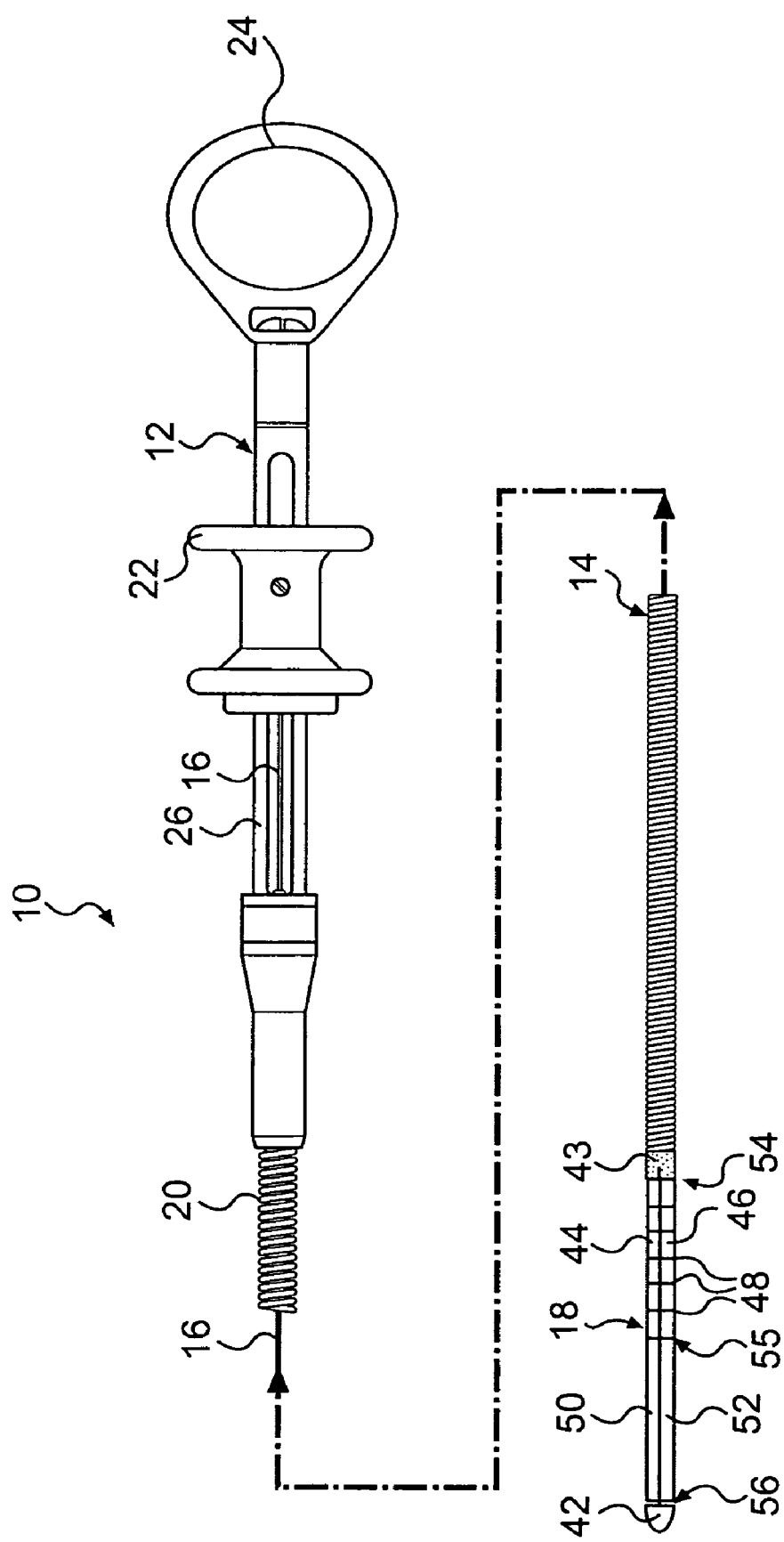
FIG. 1 is a perspective view of a DREMI in accordance with one embodiment of the present invention.

Turning to FIG. 1, the DREMI 10 is illustrated as including an actuator 12, a coil pipe 14 with an actuator wire 16, and a distal reticule 18. Actuator 12 is connected to the distal reticule by the coil pipe and actuator wire. The coil pipe and actuator wire are illustrated here in broken lines to convey the length of the DREMI. DREMI 10 will be fed through an endoscope in order to reach an internal anatomical structure. The length of the coil pipe and actuator wire must be sufficient to extend the distal reticule past the distal end of the endoscope. Coil pipe 14 might be encased by a larger outer coil pipe 20 near the actuator for increased durability. Outer coil pipe 20 would terminate at a relatively short distance in comparison to the length of coil pipe 14.

In a preferred embodiment, actuator 12 is a commonly used actuator. For instance, the illustrated actuator is available from Olympus™, and it can be used with a number of endoscopic tools. Actuator wire 16 is thread through coil pipe 14 and connects a slide 22 on actuator 12 with a distal tool, in this case distal reticule 18. The actuator body is an injection molded plastic secured, by known means, to coil pipe 14 and optional outer coil pipe 20. The actuator wire passes from slide 22 to the inside of coil pipes 14, 20 via an aperture sized and dimensioned to accept wire 16. The connection of wire 16 to slide 22 is not important for the present invention and is known in the art.

The end of actuator 12 opposite coil pipe 14 provides a thumb grip 24. In use, a user places their thumb in grip 24 with slide 22 between their index and middle fingers. Slide 22 can then be forcibly positioned along a shaft 26. Pushing slide 22 away from grip 24 (i.e., pushing wire 16 toward reticule 18) places a force at the distal end of the wire on distal reticule 18. Releasing slide 22 allows the slide to return to a natural resting position. Further discussion of the actuator 12 is not warranted here as it is a known device and operation of the actuator will be obvious to one of skill in the art. Various types of actuators are commercially available and would be suitable for use with the DREMI.

Figure 2:
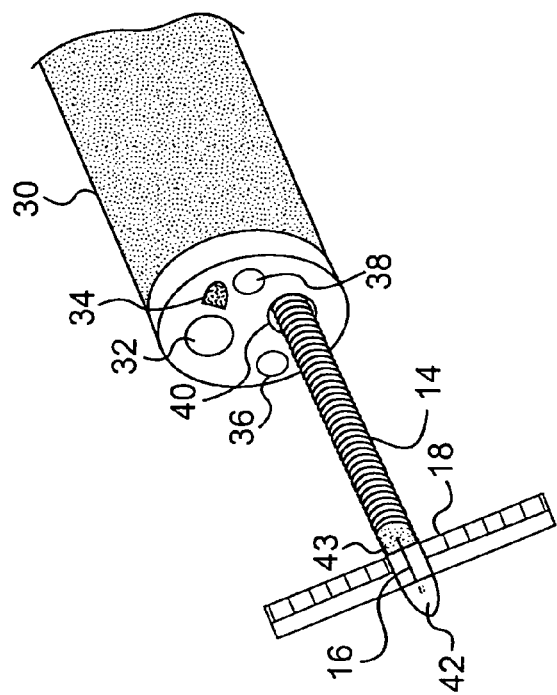
FIG. 2 is a close-up view of a DREMI in accordance with the present invention wherein the DREMI is extending out of the distal end of an endoscope.

Turning to FIG. 2, there is illustrated the distal end of an endoscope 30 with bores or lumens. The lumens act as channels for various tools or fluids. The procedure and type of endoscope both used largely determine the functionality of each lumen. For use with DREMI 10, one lumen might include a camera 32 with a lens connected by an optical fiber to a video unit (not illustrated) that displays an anatomical structure to the endoscope/DREMI operator. A secondary optical fiber 34 might be connected to a light source (not illustrated) to illuminate the structure for viewing. Lumens 36 and 38 might be fluid channels for water, air, or the like. Endoscopes often supply fluids to a structure in order to clean and dry the structure to be viewed and/or operated on. These are known endoscopic components.

A tool channel 40 is provided that allows the forward and rearward movement of DREMI 10 within endoscope 30. A valve structure (not illustrated) or other known endoscopic feature may be included to prevent fluid flow into channel 40. Of course, it would also be possible to include more or less lumen to perform additional or different tasks than described above. For instance, it is envisioned that more than one channel could be dedicated to providing a tool that extends past the end of the endoscope.

As illustrated, distal reticule 18, secured to coil pipe 14, is extended beyond the distal end of endoscope 30. Coil pipe 14 is a coiled wire, typically made from stainless steel or a thin-walled plastic tubing. The coil pipe is diminutive enough to be slidable within channel 40, but it has a sufficient diameter to allow actuator wire 16 to actuate within the coil pipe. Coil pipes and actuator wires are also used in the endoscopic art.

Returning to FIG. 1, reticule 18 consists of a molded plastic or other suitable material. As illustrated, reticule 18 is rod-shaped and it terminates at its distal end, relative to the coil pipe, at a semispherical cap 42 to which the distal end of wire 16 is anchored by conventional means. Cap 42 is an integral part of reticule 18. The proximal end of reticule 18 abuts coil pipe 14. A cap 43 is crimped onto coil pipe 14 and an anchoring portion of reticule 18 in order to secure the reticule to the coil pipe. Cap 43 can provide an optional graduation mark aligned in the direction of the folded reticule's axis (the graduation mark is illustrated but not labeled). The exact dimensions of reticule 18 are unimportant as the exact size of the DREMI, in general, will be determined by the medical procedure and/or endoscopic equipment in use.

Reticule 18 has a plurality of distinct body segments wherein each segment can be pivoted relative to any adjacent segment. A pair of upper and lower rulers 44, 46 form a substantial part of the length of reticule 18 and are parallel to each other in a folded state. The rulers have a semicircular cross section (as better illustrated in FIGS. 5 and 6). Rulers 44, 46 are proximate to the end of coil pipe 14 when reticule 18 is folded. The rulers provide graduations 48 that are placed in 1 mm increments. The graduations can be indentations, inked markings, or the like. They are visible to the DREMI operator via an endoscopic camera when the reticule is in either the folded (parallel to the axis of the endoscope) or unfolded (perpendicular to the axis of the endoscope) states, as will be discussed further below. Rulers 44, 46 are adjacent the anchored portion of the reticule.

Additional body segments include the upper backing 50 and lower backing 52. These parts of the reticule are adjacent to, and integral with, cap 42 (i.e., the distal end of DREMI 10). Backings 50, 52 are roughly the same length as upper and lower rulers 44, 46. Further, upper backing 50 is aligned with upper ruler 44 while lower backing 52 is aligned with lower ruler 46 so long as reticule 18 is in the folded state. The upper and lower backings also have semicircular cross sections. When folded, the flat side of each backing contacts the corresponding flat side of the other backing, creating a rod. The rulers are similarly arranged. When folded the backing members and rulers are aligned to create a single rod shape.

The reticule forms a rod shape that is split down the middle and held together by cap 42 (see FIGS. 5 and 6). The rulers and backings bridge the anchored portion of the reticule to cap 42. The anchored portion of the reticule are physically joined to the rulers. The rulers are physically connected to the backing members, and the backing members are physically connected to cap 42. The material between each of these sections is scored, cut, molded or otherwise constructed so as to allow the adjacent sections to pivot relative to each other. For instance, the backings pivot relative to the cap, and the anchor portion of reticule 18 (portion of reticule held to coil pipe by crimping cap 43) is also pivotally connected to the corresponding rulers.

Figure 3:
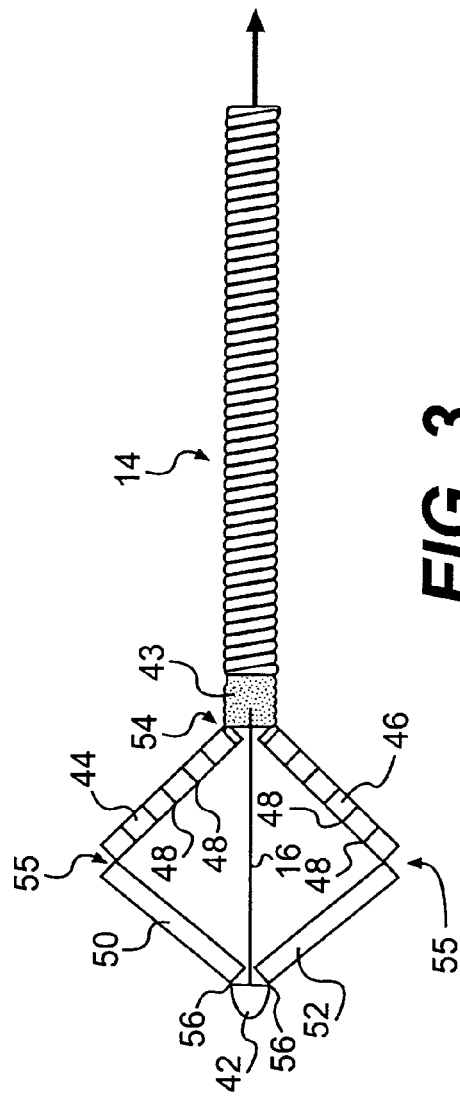
FIG. 3 is a close-up view of the distal end of a DREMI in accordance with the present invention.

Thus, the reticule has three pivot points on each side of its rod shaped body, identified in the figures as elements 54, 55, and 56. Actuating slide 22 away from its naturally biased position pulls cap 42 towards the endoscope. This causes reticule 18 to unfold along the pivot points. In this unfolded state, the body segments of the reticule are aligned substantially perpendicular to the axis of an endoscope. The unfolding action is further illustrated in FIG. 3, wherein it is illustrated that the middle of the reticule unfolds initially into a diamond shape.

Figure 4:
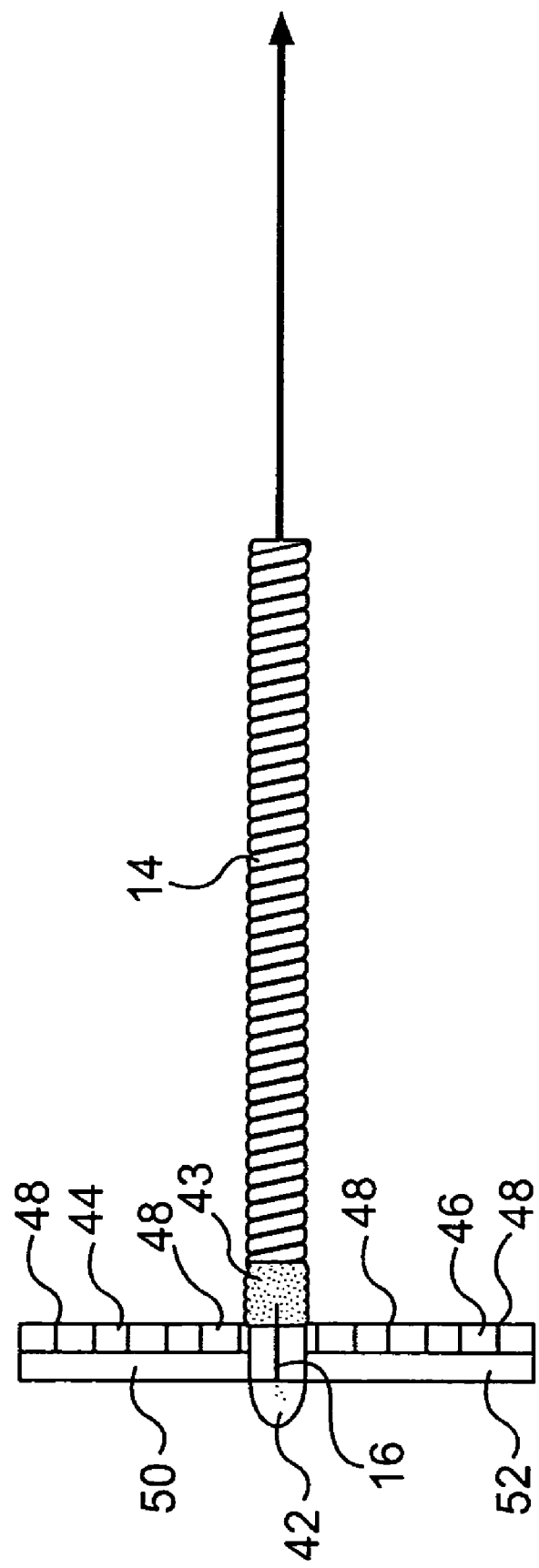
FIG. 4 is another close-up view of the distal end of a DREMI in accordance with the present invention.

The fully unfolded reticule is illustrated in FIG. 4. As will be obvious to one of skill in the art, the upper and lower rulers are aligned along an axis perpendicular to the axis of coil pipe 14 or endoscope 30. Graduations 48, placed at evenly spaced intervals along the upper and lower rulers, would be visible to an endoscopic camera. Backings 50, 52 are behind the rulers. The two backings are now aligned end-to-end. The reticule is held in the unfolded state by pressure on cap 42 in the direction of coil pipe 14. Releasing slide 22 on actuator 12 releases cap 42. The reticule returns to a folded state due to a natural biasing force. In the folded state, the reticule can be withdrawn into the endoscope.

A DREMI or endoscopic operator will, therefore, be able to pass DREMI 10 out of an endoscope so the depth of an anatomical structure could be measured while the DREMI is folded. By actuating actuator 12, the DREMI unfolds into an alignment perpendicular to the line of sight provided by the endoscopic camera. The operator can directly read the length of the same anatomical structure.

FIGS. 5 and 6 illustrate reticule 18 in further detail. Without the crimping cap 43 or wire 16 holding reticule 18 together, the two semi-spherical halves of the reticule can be spread apart to form one elongated body. FIGS. 5 and 6 both illustrate the integral relationship of the cap to the backings. The reticule is a single piece of material that is constructed or modified so as to allow for the pivot points 54, 55, 56. In one preferred embodiment, reticule 18 is a molded piece of plastic wherein the material joining all the joints 54, 55, 56 is a thin section of malleable plastic. End views for each Figure are identified as elements 60 and 62, respectively. The series of graduations 48 along the rulers are clearly evenly spaced. The anchor portion that is normally held by crimping cap 43 is labeled in these figures as element 58.

FIG. 6 illustrates the bottom side of the spread apart reticule. An axially arranged channel 64 is provided in what is normally the interior of the reticule 18. Channel 64 nests with wire 16 when reticule 18 is in the folded state. A mounting aperture 66 in cap 42 is sized and shaped to accept wire 16. The wire can be anchored to the aperture by conventional means, such as an adhesive, welding, or mechanical connection.

Assembly of the DREMI is accomplished by molding or otherwise constructing the reticule 18. Crimping cap 42 is placed over the actuator wire and positioned to partially overlap with the coilpipe. A known actuator is attached to the reticule via the actuator wire. A portion of the reticule is overlapped by crimping cap 43. A crimping force is placed on the crimping cap to hold the reticule to the coil pipe provided by the actuator. In use, an operator simply engages the actuator to fold and unfold the reticule. Other assembly techniques are available and would be obvious to one of skill in the art.

While the invention has been described with reference to specific embodiments thereof, it will be understood that numerous variations, modifications and additional embodiments are possible, and all such variations, modifications, and embodiments are to be regarded as being within the spirit and scope of the invention.

What is claimed is:

1. A direct reading endoscopic measuring instrument in an endoscopic system, the endoscopic system operable to view an internal anatomical structure, the system including an endoscope with a plurality of lumen and a distal end inserted into an anatomical structure, an endoscopic camera, the camera operable to view the interior of the anatomical structure, the direct reading endoscopic measuring instrument comprising:
   an actuator;
   an actuator wire;
   a selectively foldable distal reticule, the actuator wire connecting the actuator to the distal reticule, the actuator operable to selectively fold and unfold the distal reticule via the actuator wire, the reticule further comprising four body segments including an upper ruler, a lower ruler, an upper backing and a lower backing, the upper backing being parallel with the upper ruler and the lower backing being parallel with the lower ruler when the reticule is in a folded state, the upper backing being parallel with the lower backing and the upper ruler being parallel with the lower ruler when the reticule is in an unfolded state wherein each of the four body segments has a semicircular cross section;
   the distal reticule being movable through an endoscopic lumen in the folded state, the reticule being substantially aligned with the axis of the endoscope when in the folded state; and
   the distal reticule moveable to a position beyond the distal end of the endoscope, the distal reticule manually operable to unfold along an axis perpendicular to the axis of an endoscope when the reticule is in the unfolded state.

2. The instrument of claim 1, wherein evenly spaced graduations on the upper and lower rulers provide a means for the direct measurement of an internal anatomical structure.

3. The instrument of claim 2, wherein the graduations are visible by the endoscopic camera when the reticule is in the folded state in order to measure the depth of an anatomical structure relative to the endoscope.

4. The instrument of claim 2, wherein the graduations are visible by the endoscopic camera when the reticule is in the unfolded state in order to measure the length of an anatomical structure.

5. The instrument of claim 1, wherein evenly spaced graduations on the reticule provide a means to directly measure an internal anatomical structure, the graduations visible via the endoscopic camera when the reticule is in either the folded or unfolded states.

6. The instrument of claim 1, the selectively foldable distal reticule further comprising an end cap, the actuator wire anchored to the end cap, wherein actuation of the actuator wire pulls the end cap towards the endoscope in order to unfold the upper ruler, lower ruler, upper backing and lower backing from an alignment substantially parallel to the axis of the endoscope to an alignment perpendicular to the alignment of the endoscope.

7. A direct reading endoscopic measuring instrument comprising:
    an actuator;
    an actuator wire;
    a selectively foldable distal reticule, the reticule mechanically connected to the actuator via the actuator wire, the distal reticule providing a cap and a plurality of body segments, the actuator wire anchored to the cap; and
    wherein the reticule includes a folded state wherein the reticule is generally elongated and is substantially aligned with the actuator wire and an unfolded state wherein the reticule is perpendicular to the actuator wire, the actuator operable to unfold the plurality of body segments to the unfolded state; and
    the body segments comprising a first pair of body segments and a second pair of body segments, each body segment in the first pair of body segments and the second pair of body segments having a semicircular cross section;
    each body segment in the first pair and each body segment in the second pair being parallel to each other and the actuator wire when the reticule is in the folded state, each segment in the first pair and each segment in the second pair being parallel to each other and perpendicular to the actuator wire in the unfolded state.

8. The instrument of claim 7, wherein evenly spaced graduations on the reticule are observed to provide a direct measurement of an internal anatomical structure.

9. The instrument of claim 8, wherein the graduations are observed in the folded state in order to measure the depth of an anatomical structure.

10. The instrument of claim 8, wherein the graduations are observed in the unfolded state in order to measure the length of an anatomical structure.

11. The instrument of claim 7, wherein graduations on the reticule provide a means to directly measure an internal anatomical structure, the graduations visible via an endoscopic camera when the reticule is in either folded or unfolded states.

12. The method of operating a direct reading endoscopic measuring instrument, the method comprising:
    inserting an endoscope into a patient, the endoscope providing a tool channel and an endoscopic camera;
    moving the distal end of the endoscope to a position near an anatomical structure to be observed;
    providing a direct reading endoscopic measuring instrument providing an actuator, an actuator wire, and a distal reticule with evenly spaced graduations, the reticule comprising a first pair and a second pair of body segments; each body segment in the first pair of body segments and the second pair of body segments having a semicircular cross section
    folding the reticule so that the body segments of the first pair of body segments are parallel to each other, the body segments of the second pair of body segments are parallel to each other, and the body segments of the first pair of body segments are aligned with the body segments of the second pair of body segments;
    introducing the direct reading endoscopic measuring instrument into the endoscopic tool channel;
    maneuvering the distal reticule to a position beyond the distal end of the endoscope;
    unfolding the distal reticule through manipulation of the actuator, the step of unfolding causing the body segments of the first pair of body segments to be parallel to each other and perpendicular to the axis of the actuator wire and the body segments of the second pair of body segments to be parallel to each other and perpendicular to the axis of the actuator wire;
    viewing the graduations on the unfolded reticule in order to directly read the size of the anatomical structure.

13. The method of claim 12, further comprising the step of measuring the depth of an anatomical structure by viewing the graduations on the folded reticule wherein the reticule is adjacent to the anatomical structure.

14. The method of claim 13, further comprising steps of releasing the actuator.

* * * * *